(12) United States Patent
Mirk et al.

(10) Patent No.: US 8,598,392 B2
(45) Date of Patent: Dec. 3, 2013

(54) CONTINUOUS METHOD FOR PRODUCING SUBSTITUTED CYCLOHEXYLMETHANOLS

(75) Inventors: Daniela Mirk, Haβloch (DE); Lucia Königsmann, Stuttgart (DE); Jochem Henkelmann, Mannheim (DE)

(73) Assignee: BASF SE (DE)

( * ) Notice: Subject to any disclaimer, the term of this patent is extended or adjusted under 35 U.S.C. 154(b) by 196 days.

(21) Appl. No.: 13/140,074

(22) PCT Filed: Dec. 10, 2009

(86) PCT No.: PCT/EP2009/066834
§ 371 (c)(1),
(2), (4) Date: Jun. 16, 2011

(87) PCT Pub. No.: WO2010/079035
PCT Pub. Date: Jul. 15, 2010

(65) Prior Publication Data
US 2011/0251439 A1    Oct. 13, 2011

(30) Foreign Application Priority Data

Dec. 17, 2008 (EP) .................................... 08171922

(51) Int. Cl.
*C07C 29/19* (2006.01)
*C07C 29/20* (2006.01)
*C07C 31/135* (2006.01)

(52) U.S. Cl.
USPC ........................................................ 568/831

(58) Field of Classification Search
USPC ................................................ 568/822, 831
See application file for complete search history.

(56) References Cited

U.S. PATENT DOCUMENTS

| | | | |
|---|---|---|---|
| 3,993,604 A | 11/1976 | Thomas et al. | |
| 4,072,628 A | 2/1978 | Kruse et al. | |
| 4,181,631 A * | 1/1980 | Shaffer et al. | 512/22 |
| 4,695,660 A | 9/1987 | Otte et al. | |
| 4,847,425 A | 7/1989 | Degner et al. | |
| 6,248,924 B1 | 6/2001 | Ruhl et al. | |
| 6,268,501 B1 | 7/2001 | Kiel | |
| 6,284,917 B1 | 9/2001 | Brunner et al. | |
| 6,388,149 B2 | 5/2002 | Rühl et al. | |
| 6,441,255 B1 | 8/2002 | Haas et al. | |
| 6,888,021 B2 | 5/2005 | Brunner et al. | |
| 2004/0176549 A1 | 9/2004 | Bottcher et al. | |
| 2004/0176619 A1 | 9/2004 | Vanoppen et al. | |
| 2004/0199033 A1 | 10/2004 | Bottcher et al. | |
| 2006/0161017 A1 | 7/2006 | Grass et al. | |
| 2007/0032684 A1 * | 2/2007 | Komata et al. | 568/822 |
| 2010/0152436 A1 | 6/2010 | Laar et al. | |

FOREIGN PATENT DOCUMENTS

| | | |
|---|---|---|
| BE | 882279 A1 | 7/1980 |
| DE | 2427609 A1 | 1/1975 |
| DE | 3537228 A1 | 4/1987 |
| DE | 196 24 485 A1 | 1/1998 |
| DE | 101 28 205 A1 | 12/2002 |
| DE | 101 28 242 A1 | 12/2002 |
| EP | 0293739 A1 | 12/1988 |
| EP | 0 814 098 A2 | 12/1997 |
| EP | 0992475 A2 | 4/2000 |
| EP | 1004564 A1 | 5/2000 |
| EP | 1090902 A2 | 4/2001 |
| EP | 1676829 A2 | 7/2006 |
| JP | 62185032 A | 8/1987 |
| KR | 20040072433 A | 8/2004 |
| WO | WO-99/32427 A1 | 7/1999 |
| WO | WO-02/100536 A1 | 12/2002 |
| WO | WO-02/100538 A2 | 12/2002 |
| WO | WO-2006/136541 A2 | 12/2006 |

OTHER PUBLICATIONS

Alvin B. Stiles et al., "Catalyst Manufacture", pp. 177-187, 1995.
Benoît Heinrich et al., "Sol-Gel Syntheses of Supported Metals", Catalyst Preparation: Science and Engineering, Chapter 8, pp. 163-208, edited by J. Regalbuto, (2007).
International Search Report for PCT EP2009/066834 mailed Jul. 2, 2010.

* cited by examiner

*Primary Examiner* — Brian J Davis
(74) *Attorney, Agent, or Firm* — Novak Druce Connolly Bove + Quigg LLP

(57) ABSTRACT

The present invention relates to a continuous process for preparing para-alkyl-substituted cyclohexylmethanols, especially 4-isopropylcyclohexylmethanol, by catalytically hydrogenating the corresponding aldehydes or ketones in the presence of hydrogen and in the presence of a catalyst which comprises, as an active metal, ruthenium applied to a support, the support comprising $Al_2O_3$ and/or $SiO_2$, and the catalyst being used in the form of a fixed bed catalyst in a hydrogenation reactor or in a plurality of hydrogenation reactors connected in series.

11 Claims, No Drawings

CONTINUOUS METHOD FOR PRODUCING SUBSTITUTED CYCLOHEXYLMETHANOLS

CROSS-REFERENCE TO RELATED APPLICATIONS

This application is a national stage application (under 35 U.S.C. §371) of PCT/EP2009/066834, filed Dec. 10, 2009, which claims benefit of European application 08171922.1, filed Dec. 17, 2008.

BACKGROUND OF THE INVENTION

The present invention relates to a continuous process for preparing para-alkyl-substituted cyclohexylmethanols, especially 4-isopropylcyclohexylmethanol, by catalytically hydrogenating the corresponding aldehydes or ketones in the presence of hydrogen and of a supported ruthenium catalyst.

4-Alkyl- or -alkenyl-substituted cyclohexylmethanols and the ethers and esters thereof are valuable aroma chemicals which, owing to their lily of the valley-like fragrance, find wide use in the aromatization of everyday or consumable goods of all kinds. A compound which is particularly sought-after in this respect is 4-isopropylcyclohexyl-methanol, which is typically used in the form of a mixture of its cis and trans isomers and is sold under the trade name Mayol® (Firmenich SA, Geneva).

Owing to the constantly rising demand for the aroma chemicals mentioned, specifically for 4-isopropylcyclohexylmethanol, it is becoming ever more difficult for the existing processes for preparing the compounds mentioned to be able to meet this demand. There is therefore a need for a high-performance preparation process for the compounds mentioned which is suitable for preparation on the industrial scale, especially for the preparation of 4-isopropylcyclohexylmethanol.

DE 24 27 609 discloses alicyclic cyclohexylmethanols, and the ethers or esters thereof, which have an isopropyl or isopropenyl radical in the 4 position, and the use thereof as odorants or flavorings. In addition, the document discloses processes for preparing the compounds mentioned by catalytically hydrogenating correspondingly unsaturated starting compounds. By way of example, the preparation of 4-isopropylcyclohexyl-methanol by catalytic hydrogenation of cuminaldehyde in 1,2-dimethoxyethane as a solvent and in the presence of a ruthenium-carbon catalyst with a ruthenium content of 5% is described. The reaction was performed at a pressure of 100 atmospheres and at a temperature of 130° C. and afforded, after fractional distillation of the crude product, 4-isopropylcyclohexylmethanol in the form of a mixture of 70:30 parts by weight of the cis and trans isomers.

EP 0 293 739 relates to a process for preparing 4-isopropylcyclohexylmethanol or alkyl ethers thereof by ring hydrogenation of 4-(1-alkoxy-1-methylethyl)benzaldehydes or of dialkyl acetals thereof in the presence of noble metals of group VIII of the periodic table, for example nickel, palladium, platinum, rhodium and ruthenium. The metals mentioned may be applied to a catalyst support material, for example aluminum oxide or activated carbon, in amounts of from 0.5 to 10% by weight, or else be used in the form of the pure metals or metal compounds. The reactions are performed under hydrogen pressures of from 50 to 350 bar and at temperatures of from 100 to 250° C.

EP 0 992 475 discloses a process for preparing an alcohol by catalytically hydrogenating the corresponding aldehyde, excluding 3-hydroxypropionaldehyde, or ketone in aqueous or organic solution at a temperature of from 20 to 200° C. and an $H_2$ pressure of from 0.5 to 30 MPa using a support-bound ruthenium catalyst, wherein the catalyst used is ruthenium on an oxidic support from the group of $TiO_2$, $SiO_2$, $ZrO_2$, MgO, mixed oxides and silicates, excluding zeolites, with an Ru content of from 0.1 to 20% by weight. The use of $TiO_2$ and $SiO_2$ as support materials achieves high service lives of the catalyst, but ring hydrogenation of aromatic substrates is not described.

EP 1 004 564 relates to a process for preparing hydroxyethylcyclohexanes by catalytically hydrogenating the corresponding hydroxyethylbenzenes by means of ruthenium as a catalyst, which has been treated with a reducing agent before use. The process is performed in an alkane with a boiling point of more than 70° C. as a solvent.

KR 2004072433 discloses a process for preparing 1-cyclohexyl-1-ethanol by continuously hydrogenating 1-methylbenzyl alcohol and/or acetophenone over a silica gel-supported ruthenium catalyst with a ruthenium content of from 1 to 5% by weight, the silica gel support having an "acid activity index" of less than 10%.

EP 1 676 829 relates to a process for continuously catalytically hydrogenating hydrogenatable compounds, specifically aromatic carboxylic acids or derivatives thereof, which are ring-hydrogenated. In the reaction, which is effected over solid catalysts arranged in a fixed bed with a hydrogenous gas, the hydrogenation is performed in at least two hydrogenation units connected in series, and at least one of the two hydrogenation units is operated in loop mode, using, for the hydrogenation units, catalyst volumes which are obtainable by a specific determination process.

BRIEF SUMMARY OF THE INVENTION

Proceeding from this prior art, it was an object of the present invention to provide a continuous process for preparing 4-isopropylcyclohexylmethanol and closely related compounds, which enables the desired target compound to be obtained
- proceeding from very inexpensive and readily available starting materials,
- in maximum yield and high chemical purity,
- in very substantially diastereomerically enriched form,
- with a maximum content of the desired cis isomer,
- with a minimal and readily removable by-product spectrum,
- in a very simple manner in terms of process technology,
- using a very inexpensive catalyst and
- very substantially dispensing with solvents and other additives or reagents.

The object was achieved in accordance with the invention by the provision of a continuous process for preparing a 1-hydroxyalkylcyclohexane of the formula (I)

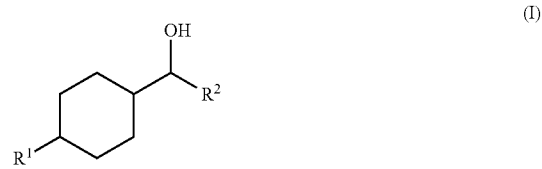

(I)

where
$R^1$ is hydrogen or a straight-chain or branched alkyl radical having from 1 to 4 carbon atoms and
$R^2$ is hydrogen or a straight-chain or branched alkyl radical having from 1 to 3 carbon atoms, by catalytically hydrogenating an aromatic carbonyl compound of the formula (II)

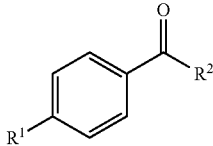
(II)

and/or by catalytically hydrogenating an aromatic alcohol of the formula (III)

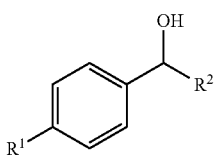
(III)

in which the $R^1$ and $R^2$ radicals are each as defined in formula (I),
in the presence of hydrogen and in the presence of a catalyst which comprises, as an active metal, ruthenium applied to a support, the support comprising $Al_2O_3$ and/or $SiO_2$, and the catalyst being used in the form of a fixed bed catalyst in a hydrogenation reactor or in a plurality of hydrogenation reactors connected in series.

DETAILED DESCRIPTION OF THE INVENTION

The starting material used to perform the process according to the invention may, as desired, be the aromatic aldehydes or ketones of the formula (II) and/or the aromatic alcohols of the formula (III).

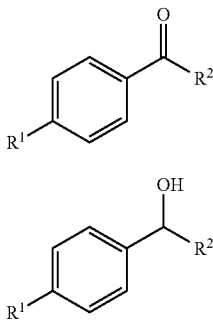
(II)

(III)

The aromatic starting compounds mentioned may be unsubstituted in the para position of the aromatic or bear a straight-chain or branched alkyl radical having from 1 to 4 carbon atoms. The $R^1$ radical is preferably a straight-chain or branched alkyl radical having from 1 to 4 carbon atoms, for example methyl, ethyl, n-propyl, isopropyl, n-butyl, sec-butyl or tert-butyl. The $R^1$ radical is more preferably a straight-chain or branched alkyl radical having from 1 to 3 carbon atoms. Especially preferably, the $R^1$ radical is isopropyl.

The $R^2$ radical in the compounds of the formulae (II) and (III) usable in accordance with the invention may be hydrogen or a straight-chain or branched and alkyl radical having from 1 to 3 carbon atoms, such as methyl, ethyl, n-propyl or isopropyl. The $R^2$ radical is preferably hydrogen.

The compounds of the formulae (II) and (III) mentioned can be used as desired in the process according to the invention, though, when the $R^1$ and $R^2$ radicals are defined identically in each case, the same target compound of the formula (I) is obtained, in which the radicals mentioned are each as defined as in the starting compound(s). Accordingly, the compounds of the formulae (II) and (III), when the particular $R^1$ and $R^2$ radicals are defined identically, may be used alone, i.e. in pure form, or in the form of mixtures with one another.

In a preferred embodiment, the process according to the invention is performed only using aromatic carbonyl compounds, i.e. aldehydes or ketones of the formula (II). Starting compounds which are preferred in turn are the compounds of the formula (II) in which the $R^2$ radical is hydrogen. Particularly preferred starting compounds are the para-substituted benzaldehydes of the formula (II) in which the $R^2$ radical is hydrogen and the $R^1$ radical is methyl, ethyl, n-propyl, isopropyl, n-butyl, sec-butyl or tert-butyl, more preferably isopropyl.

A starting compound especially preferred in accordance with the invention is accordingly the para-isopropylbenzaldehyde of the formula (IIa)

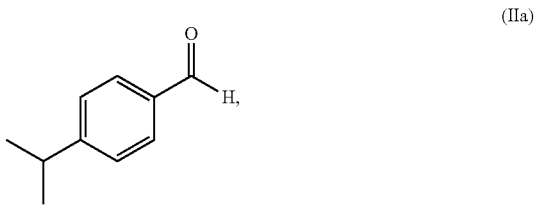
(IIa)

which is also known as cuminaldehyde.

The products of the process according to the invention obtained from the selected starting compounds are the 1-hydroxyalkylcyclohexanes of the formula (I)

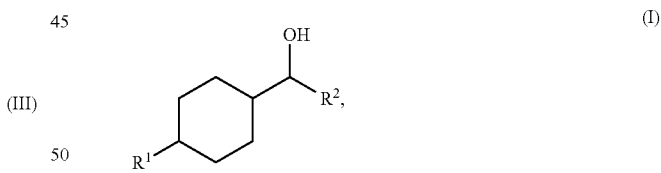
(I)

where the $R^1$ and $R^2$ radicals have the same definitions or preferred definitions as described for the formulae (II) and (III). Possible process products are accordingly the cycloaliphatic compounds of the formula (I) in which the $R^1$ radical is a straight-chain or branched alkyl radical having from 1 to 4 carbon atoms, for example methyl, ethyl, n-propyl, isopropyl, n-butyl, sec-butyl or tert-butyl. The $R^1$ radical in formula (I) is more preferably isopropyl.

The $R^2$ radical in formula (I) may be hydrogen or a straight-chain or branched and alkyl radical having from 1 to 3 carbon atoms, such as methyl, ethyl, n-propyl or isopropyl. The $R^2$ radical in formula (I) is preferably hydrogen. A process product particularly preferred in accordance with the invention is therefore 4-isopropylcyclohexylmethanol of the formula (Ia)

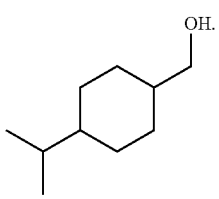

(Ia)

The cycloaliphatic compounds of the formulae (I) and (Ia) mentioned may, based on the relative configuration of the two radicals in the 1 and 4 positions of the cyclohexyl ring, be present in the form of the trans isomer of the formula (Ib)

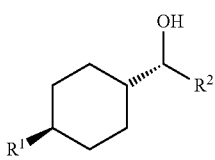

(Ib)

and in the form of the cis isomer of the formula (Ic)

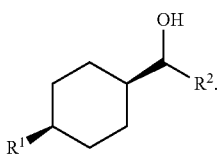

(Ic)

According to the invention, the stereoisomers mentioned are generally obtained in the form of mixtures of the particular cis and trans isomers.

In the process according to the invention, the $R^1$ and $R^2$ radicals of the starting materials of the formulae (II) and (III) are preserved, provided that they are not impaired by undesired side reactions. In the course of the process according to the invention, only the hydrogenation of the aromatic ring of the selected compound of the formula (II) and/or (III) to the cycloaliphatic cyclohexyl ring and, in the case of use of aldehydes or ketones of the formula (II), a reduction of the carbonyl group to the corresponding alcohol group, take place.

The process according to the invention is performed in the presence of hydrogen and in the presence of a catalyst which comprises, as an active metal, ruthenium applied to a support, the support comprising $Al_2O_3$ and/or $SiO_2$ or preferably consisting of $Al_2O_3$ or $SiO_2$. Catalysts usable in accordance with the invention may comprise ruthenium as an active metal alone or together with at least one further metal of transition groups IB, VIIB or VIII of the Periodic Table of the Elements (CAS version). Such catalysts are known and are described, for example, in EP 0 814 098, WO 99/32427, WO 02/100536 and WO 2006/136541, to which explicit reference is made on this subject.

The catalysts for use in accordance with the invention are used in the form of a fixed bed catalyst and have $Al_2O_3$ and/or $SiO_2$ at least as main constituents of the supports, the support materials mentioned being usable in principle in all to the person skilled in the art as suitable forms or polymorphs. For example, $Al_2O_3$ can be used in the alpha, delta, theta, or gamma polymorph. The support materials selected can then be treated in a manner known per se with a suitable ruthenium compound and optionally with one or more further compounds of metals of transition groups IB, VIIB or VIII of the Periodic Table of the Elements. Such preparation processes are known and are described comprehensively, for example, in Catalyst Preparation, edited by J. Regalbuto, (2007), p. 177 or Catalyst Manufacture, A. B. Stiles, T. A. Koch, (1995), p. 377, and, for example, in DE-A 101 282 05 and DE-A 101 282 42 and also DE 196 244 85. In a preferred embodiment, the process according to the invention is performed in the presence of a catalyst, i.e. of a fixed bed catalyst, which comprises only $SiO_2$ as a support.

The supported catalysts for use in accordance with the invention generally have a ruthenium content of from 0.001 to 20% by weight, preferably from 0.01 to 10% by weight, more preferably from 0.1 to 5% by weight and even more preferably from 0.1 to 4% by weight, 3% by weight, 2% by weight or even more preferably to 1% by weight (based in each case on the total weight of the finished, ready-to-use catalyst).

In an especially preferred embodiment of the process according to the invention, a fixed bed catalyst which, based on the total weight of the finished catalyst, has a ruthenium content of from 0.1 to 0.8% by weight, even more preferably to 0.7% by weight, 0.6% by weight, and especially preferably from 0.1 to 0.5% by weight is used.

In the context of the present invention, the term "fixed bed" should be interpreted widely, as described, for example, in Römpp Online, Version 3.3, Georg Thieme Verlag, 2008. Accordingly, a fixed bed is typically a support of large surface area which has been provided with a catalyst and fixed in the interior of a fixed bed reactor. Gases and/or liquids (fluids) to be reacted typically flow through the reactor; the reaction takes place over the catalyst. The support may be a layer (bed, packing) of a fine particulate solid (support material: particles, spheres, pellets, etc.), a tube bundle, a structured packing, etc. Further explanations can also be found, for example, under G. Eigenberger, "Fixed-bed Reactors" in Ullmann's Encyclopedia of Industrial Chemistry 7th Edition (electronic encyclopedia).

In the case of use of a fixed bed reactor which comprises $SiO_2$ as the support material, especially the coated catalysts disclosed in WO 2006/136541 have been found to be advantageous in the process according to the invention. Such coated catalysts comprise, as an active metal, ruthenium alone or together with at least one further metal of transition groups IB, VIIB or VIII of the Periodic Table of the Elements (CAS version), applied to a support comprising silicon dioxide as a support material.

In this coated catalyst usable with preference in accordance with the invention, the amount of the active metal is <1% by weight, preferably from 0.1 to 0.5% by weight, more preferably from 0.25 to 0.35% by weight, based on the total weight of the catalyst, and at least 60% by weight, more preferably 80% by weight, of the active metal, based on the total amount of the active metal, is present in the coating of the catalyst up to a penetration depth of 200 µm. The aforementioned data are determined by means of SEM (scanning electron microscopy) EPMA (electron probe microanalysis)—EDXS (energy dispersive X-ray spectroscopy) and are averaged values. Further information regarding the aforementioned analysis methods and techniques are disclosed, for example, in "Spectroscopy in Catalysis" by J. W. Niemantsverdriet, VCM, 1995.

The coated catalyst usable with preference in accordance with the invention is notable in that the predominant amount of the active metal is present in the coating up to a penetration depth of 200 µm, i.e. close to the surface of the coated catalyst.

In contrast, only a very small amount, if any, of the active metal is present in the interior (core) of the catalyst. It has been found that, surprisingly, the catalyst usable with preference in accordance with the invention—in spite of the small amount of active metal—has a very high activity in the hydrogenation of the starting compounds of the formulae (II) and (III) to be converted in accordance with the invention, coupled with very good selectivities. More particularly, the activity of the inventive catalyst does not decrease over a long hydrogenation period.

Very particular preference is given to an inventive coated catalyst in which no active metal can be detected in the interior of the catalyst, i.e. active metal is present only in the outermost coating, for example in a zone up to a penetration depth of 100-200 μm.

In a further particularly preferred embodiment, the coated catalyst for use with preference in accordance with the invention is notable in that, in (FEG)-TEM (Field Emission Gun-Transmission Electron Microscopy) with EDXS, active metal particles can be detected only in the outermost 200 μm, preferably 100 μm, most preferably 50 μm (penetration depth). Particles smaller than 1 nm cannot be detected.

The active metal used may be ruthenium alone or together with at least one further metal of transition groups IB, VIIB or VIII of the Periodic Table of the Elements (CAS version). Suitable further active metals in addition to ruthenium are, for example, platinum, rhodium, palladium, iridium, cobalt or nickel or a mixture of two or more thereof. Among the metals of transition groups IB and/or VIIB of the Periodic Table of the Elements which can likewise be used, suitable metals are, for example, copper and/or rhenium. Preference is given to using ruthenium alone as the active metal or together with platinum or iridium in the inventive coated catalyst; very particular preference is given to using ruthenium alone as the active metal.

The coated catalyst usable in accordance with the invention exhibits the aforementioned very high activity at a low loading with active metal which is <1% by weight based on the total weight of the catalyst. The amount of the active metal in the inventive coated catalyst is preferably from 0.1 to 0.5% by weight, more preferably from 0.25 to 0.35% by weight. It has been found that the penetration depth of the active metal into the support material is dependent upon the loading of the catalyst with active metal. Even in the case of loading of the catalyst with 1% by weight or more, for example in the case of loading with 1.5% by weight, a substantial amount of active metal is present in the interior of the catalyst, i.e. in a penetration depth of from 300 to 1000 μm, which impairs the activity of the hydrogenation catalyst, especially the activity over a long hydrogenation period, especially in the case of rapid reactions, where hydrogen deficiency can occur in the interior of the catalyst (core).

In the coated catalyst for use with preference in accordance with the invention, at least 60% by weight of the active metal, based on the total amount of the active metal, is present in the coating of the catalyst up to a penetration depth of 200 μm. In the coated catalyst usable in accordance with the invention, preferably at least 80% by weight of the active metal, based on the total amount of the active metal, is present in the coating of the catalyst up to a penetration depth of 200 μm. Very particular preference is given in accordance with the invention to using a coated catalyst in which no active metal can be detected in the interior of the catalyst, i.e. active metal is present only in the outermost coating, for example in a zone up to a penetration depth of 100-200 μm. In a further preferred embodiment, 60% by weight, preferably 80% by weight, based on the total amount of the active metal, is present in the coating of the catalyst up to a penetration depth of 150 μm.

The aforementioned data are determined by means of SEM (scanning electron microscopy) EPMA (electron probe microanalysis)—EDXS (energy dispersive X-ray spectroscopy) and constitute average values. To determine the penetration depth of the active metal particles, a plurality of catalyst particles (for example 3, 4 or 5) are abraded transverse to the extrudate axis (when the catalyst is present in the form of extrudates). By means of line scans, the profiles of the active metal/Si concentration ratios are then recorded. On each measurement line, a plurality of, for example 15-20, measurement points are measured at equal intervals; the measurement spot size is approx. 10 μm*10 μm. After integration of the amount of active metal over the depth, the frequency of the active metal in a zone can be determined.

Most preferably, the amount of the active metal, based on the concentration ratio of active metal to Si, on the surface of the coated catalyst for use with preference is from 2 to 25%, preferably from 4 to 10%, more preferably from 4 to 6%, determined by means of SEM EPMA-EDXS. The surface is analyzed by means of analyses of regions of 800 μm×2000 μm and with an information depth of approx. 2 μm. The elemental composition is determined in % by weight (normalized to 100%). The mean concentration ratio (active metal/Si) is averaged over 10 measurement regions.

In the context of the present application, the surface of the coated catalyst is understood to mean the outer coating of the catalyst up to a penetration depth of approx. 2 μm. This penetration depth corresponds to the information depth in the aforementioned surface analysis.

Very particular preference is given to using a coated catalyst in which the amount of the active metal, based on the weight ratio of active metal to Si (wt./wt. in %), on the surface of the coated catalyst is from 4 to 6%, from 1.5 to 3% in a penetration depth of 50 μm and from 0.5 to 2% in the region of penetration depth from 50 to 150 μm, determined by means of SEM EPMA (EDXS). The values stated constitute averaged values.

Moreover, the size of the active metal particles preferably decreases with increasing penetration depth, determined by means of (FEG)-TEM analysis.

The active metal is present in the inventive coated catalyst preferably partly or fully in crystalline form. In preferred cases, ultrafine crystalline active metal can be detected in the coating of the inventive coated catalyst by means of SAD (Selected Area Diffraction) or XRD (X-Ray Diffraction).

The coated catalyst usable with preference in accordance with the invention may additionally comprise alkaline earth metal ions ($M^{2+}$), i.e. M=Be, Mg, Ca, Sr and/or Ba, in particular Mg and/or Ca, most preferably Mg. The content of alkaline earth metal ion(s) ($M^{2+}$) in the catalyst is preferably from 0.01 to 1% by weight, in particular from 0.05 to 0.5% by weight, very particularly from 0.1 to 0.25% by weight, based in each case on the weight of the silicon dioxide support material.

An essential constituent of the coated catalysts usable with preference in accordance with the invention is the support material based on silicon dioxide, generally amorphous silicon dioxide. In this context, the term "amorphous" is understood to mean that the proportion of crystalline silicon dioxide phases makes up less than 10% by weight of the support material. However, the support materials used to prepare the catalysts may have superstructures which are formed by regular arrangement of pores in the support material.

Useful support materials in the case of use of the coated catalysts usable with preference in accordance with the invention are in principle amorphous silicon dioxide types which consist of silicon dioxide at least to an extent of 90% by weight, and the remaining 10% by weight, preferably not more than 5% by weight, of the support material may also be another oxidic material, for example MgO, CaO, $TiO_2$, $ZrO_2$, $Fe_2O_3$ and/or alkali metal oxide.

In a preferred embodiment of the invention, the support material is halogen-free, especially chlorine-free, i.e. the content of halogen in the support material is less than 500 ppm by weight, for example in the range from 0 to 400 ppm by weight. Preference is thus given to a coated catalyst which comprises less than 0.05% by weight of halide (determined by ion chromatography) based on the total weight of the catalyst.

Preference is given to support materials which have a specific surface area in the range from 30 to 700 $m^2/g$, preferably from 30 to 450 $m^2/g$ (BET surface area to DIN 66131).

Suitable amorphous support materials based on silicon dioxide are familiar to those skilled in the art and commercially available (see, for example, O. W. Flörke, "Silica" in Ullmann's Encyclopedia of Industrial Chemistry $6^{th}$ Edition on CD-ROM). They may be either of natural origin or have been synthetically produced. Examples of suitable amorphous support materials based on silicon dioxide are silica gels, kieselguhr, fumed silicas and precipitated silicas. In a preferred embodiment of the invention, the catalysts have silica gels as support materials.

According to the configuration of the coated catalyst for use in accordance with the invention, the support material may have a different shape. When the inventive coated catalyst is used in fixed catalyst beds, as in the context of the present invention, use is typically made of moldings of the support material which are obtainable, for example, by extruding or tableting, and which may have, for example, the shape of spheres, tablets, cylinders, extrudates, rings or hollow cylinders, stars and the like. The dimensions of these moldings vary typically within the range from 0.5 mm to 25 mm. Frequently, catalyst extrudates with extrudate diameters of from 1.0 to 5 mm and extrudate lengths of from 2 to 25 mm are used. It is generally possible to achieve higher activities with smaller extrudates; however, these often do not have sufficient mechanical stability in the hydrogenation process. Very particular preference is therefore given to using extrudates with extrudate diameters in the range from 1.5 to 3 mm.

The coated catalysts usable with preference in accordance with the invention are prepared preferably by first impregnating the support material once or more than once with a solution of ruthenium(III) acetate alone or together with a solution of at least one further salt of metals of transition groups IB, VIIB or VIII of the Periodic Table of the Elements (CAS version), drying the resulting solid and subsequent reduction, the solution of the at least one further salt of metals of transition groups IB, VIIB or VIII of the Periodic Table of the Elements being applicable in one or more impregnation steps together with the solution of ruthenium(III) acetate or in one or more combined impregnation steps separately from the solution of ruthenium(III) acetate. The individual process steps are described in detail below and comprise the steps of:

i) impregnating the support material comprising silicon dioxide once or more than once with a solution of ruthenium(III) acetate alone or together with a solution of at least one further salt of metals of transition groups IB, VIIB or VIII of the Periodic Table of the Elements (CAS version);

ii) subsequent drying;

iii) subsequent reduction;

the solution of the at least one further salt of metals of transition groups IB, VIIB or VIII of the Periodic Table of the Elements being applicable in one or more impregnation steps together with the solution of ruthenium(III) acetate or in one or more impregnation steps separately from the solution of ruthenium(III) acetate.

Step i)

In step i), the support material comprising silicon dioxide is impregnated once or more than once with a solution of ruthenium(III) acetate alone or together with at least one further dissolved salt of metals of transition groups IB, VIIB or VIII of the Periodic Table of the Elements (CAS version). Since the amount of active metal in the inventive coated catalyst is very small, a simple impregnation is effected in a preferred embodiment. Ruthenium(III) acetate and the salts of metals of transition groups IB, VIIB or VIII of the Periodic Table of the Elements constitute active metal precursors. It has been found that, surprisingly, in the case of use of ruthenium(III) acetate as a precursor, it is possible to obtain coated catalysts which are notable, among other features, in that the significant portion of the active metal, preferably ruthenium alone, is present in the coated catalyst up to a penetration depth of 200 μm. The interior of the coated catalyst has only little active metal, if any. When, in contrast, ruthenium(III) nitrosylnitrate is used as a precursor, as disclosed in the examples in DE-A 101 28 205 and DE-A 101 28 242, a ruthenium catalyst is obtained, which comprises ruthenium distributed homogeneously over the catalyst down to slightly depleted in the interior of the catalyst.

Suitable solvents for providing the solution of ruthenium (III) acetate or the solution of at least one further salt of metals of transition groups IB, VIIB or VIII of the Periodic Table of the Elements are water or else mixtures of water or solvent with up to 50% by volume of one or more water- or solvent-miscible organic solvents, for example mixtures with $C_1$-$C_4$-alkanols such as methanol, ethanol, n-propanol or isopropanol. Aqueous acetic acid or glacial acetic acid may likewise be used. All mixtures should be selected such that a solution or phase is present. Preferred solvents are acetic acid, water or mixtures thereof. Particular preference is given to using a mixture of water and acetic acid as a solvent, since ruthenium (III) acetate is typically present dissolved in acetic acid or glacial acetic acid. However, ruthenium(III) acetate may also be used as a solid after dissolution. The inventive catalyst may also be prepared without use of water.

The solution of the at least one further salt of metals of transition groups IB, VIIB or VIII of the Periodic Table of the Elements can be applied in one or more impregnation steps together with the solution of ruthenium(III) acetate or in one or more impregnation steps separately from the solution of ruthenium(III) acetate. This means that the impregnation can be effected with one solution which comprises ruthenium(III) acetate and also at least one further salt of metals of transition groups IB, VIIB or VIII of the Periodic Table of the Elements. The impregnation with this solution can be effected once or more than once. However, it is likewise possible that impregnation is effected first with a ruthenium(III) acetate solution and then, in a separate impregnation step, with a solution which comprises at least one further salt of metals of transition groups IB, VIIB or VIII of the Periodic Table of the Elements. The sequence of the impregnation steps may also be reversed. It is likewise possible that one of the two impregnation steps or both impregnation steps are repeated once or more than once in any sequence. Each impregnation step is typically followed by drying.

Suitable salts of further metals of transition groups IB, VIIB or VIII of the Periodic Table of the Elements which can be used in the impregnation step are, for example, nitrates, acetonates and acetates, preference being given to acetates.

Particular preference is given to effecting impregnation with a solution of ruthenium(III) acetate alone in one impregnation step.

The impregnation of the support material can be effected in different ways and depends in a known manner upon the form of the support material. For example, the support material can be sprayed or flushed with the precursor solution or the support material can be suspended in the precursor solution. For example, the support material can be suspended in an aqueous solution of the active metal precursor and, after a certain time, filtered off from the aqueous supernatant. The amount of liquid absorbed and the active metal concentration of the solution can then be used to control the active metal content of the catalyst in a simple manner. The support material can also be impregnated by, for example, treating the support with a defined amount of the solution of the active metal precursor which corresponds to the maximum amount of liquid that the support material can absorb. For this purpose, the support material can, for example, be sprayed with the required amount of liquid. Suitable apparatus for this purpose is the apparatus used customarily for mixing liquids with solids (see Vauck/Müller, Grundoperationen chemischer Verfahrenstechnik [Basic Operations in Chemical Process Technology], 10th edition, Deutscher Verlag für Grundstoffindustrie, 1994, p. 405 ff.), for example tumble driers, impregnating drums, drum mixers, paddle mixers and the like. Monolithic supports are typically flushed with the aqueous solutions of the active metal precursor.

The solutions used for impregnation are preferably low-halogen, especially low-chlorine, i.e. they comprise no or less than 500 ppm by weight, especially less than 100 ppm by weight of halogen, for example from 0 to <80 ppm by weight of halogen based on the total weight of the solution.

The concentration of the active metal precursor in the solutions depends, by its nature, upon the amount of active metal precursor to be applied and the absorption capacity of the support material for the solution and is <20% by weight, preferably from 0.01 to 6% by weight, more preferably from 0.1 to 1.1% by weight, based on the total mass of the solution used.

Step ii)

The drying can be effected by customary processes for drying solids while maintaining the upper temperature limits specified below. The maintenance of the upper limit of the drying temperatures is important for the quality, i.e. the activity, of the catalyst. Exceedance of the drying temperatures specified below leads to a distinct loss of activity. Calcination of the support at higher temperatures, for example above 300° C. or even 400° C., as the prior art proposes, is not only superfluous but also has a disadvantageous effect on the activity of the catalyst. To achieve sufficient drying rates, the drying is effected preferably at elevated temperature, preferably at ≤180° C., particularly at ≤160° C., and at least 40° C., in particular at least 70° C., especially at least 100° C., very particularly in the range from 110° C. to 150° C.

The solid impregnated with the active metal precursor is dried typically under standard pressure, and the drying can also be promoted by employing reduced pressure. Frequently, the drying will be promoted by passing a gas stream over or through the material to be dried, for example air or nitrogen.

The drying time depends, by its nature, upon the desired degree of drying and the drying temperature and is preferably in the range from 1 h to 30 h, preferably in the range from 2 to 10 h.

The drying of the treated support material is preferably conducted to such an extent that the content of water or of volatile solvent constituents before the subsequent reduction makes up less than 5% by weight, in particular not more than 2% by weight, based on the total weight of the solid. The proportions by weight specified relate to the weight loss of the solid, determined at a temperature of 160° C., a pressure of 1 bar and a time of 10 min. In this way, the activity of the catalysts used in accordance with the invention can be enhanced further.

Step iii)

The solid obtained after the drying is converted to its catalytically active form by reducing the solid at temperatures in the range of generally from 150° C. to 450° C., preferably from 250° C. to 350° C., in a manner known per se.

For this purpose, the support material is contacted with hydrogen or a mixture of hydrogen and an inert gas at the above-specified temperatures. The absolute hydrogen pressure is of minor importance for the result of the reduction and can, for example, be varied within the range from 0.2 bar to 1.5 bar. Frequently, the catalyst material is hydrogenated at standard hydrogen pressure in a hydrogen stream. Preference is given to effecting the reduction with movement of the solid, for example by reducing the solid in a rotary tube oven or a rotary sphere oven. In this way, the activity of the inventive catalysts can be enhanced further. The hydrogen used is preferably free of catalyst poisons such as compounds comprising CO and S, for example $H_2S$, COS and others.

The reduction can also be effected by means of organic reducing reagents such as hydrazine, formaldehyde, formates or acetates.

After the reduction, the catalyst can be passivated in a known manner to improve the handling, for example by treating the catalyst briefly with an oxygen-containing gas, for example air, but preferably with an inert gas mixture comprising from 1 to 10% by volume of oxygen. It is also possible here to use $CO_2$ or $CO_2/O_2$ mixtures.

The active catalyst may also be stored under an inert organic solvent, for example ethylene glycol.

To prepare the coated catalyst for use with preference in accordance with the invention, in a further embodiment, the active metal catalyst precursor, for example prepared as above or prepared as described in WO-A2-02/100538 (BASF AG), can be impregnated with a solution of one or more alkaline earth metal(II) salts.

Preferred alkaline earth metal(II) salts are corresponding nitrates, especially magnesium nitrate and calcium nitrate.

The preferred solvent for the alkaline earth metal(II) salts in this impregnation step is water. The concentration of the alkaline earth metal(II) salt in the solvent is, for example, from 0.01 to 1 mol/liter.

For example, the active metal/$SiO_2$ catalyst installed in a tube is contacted with a stream of an aqueous solution of the alkaline earth metal salt. The catalyst to be impregnated may also be treated with a supernatant solution of the alkaline earth metal salt.

This preferably results in saturation of the active metal/$SiO_2$ catalyst, especially of its surface, with the alkaline earth metal ion(s) taking place.

Excess alkaline earth metal salt and unimmobilized alkaline earth metal ions is/are flushed from the catalyst ($H_2O$ rinsing, catalyst washing).

For simplified handling, for example installation in a reactor tube, the catalyst for use with preference in accordance with the invention can be dried after the impregnation. For this purpose, the drying can be carried out, for example, in an oven at <200° C., for example at from 50 to 190° C., more preferably at <140° C., for example at from 60 to 130° C.

This impregnation process can be carried out ex situ or in situ ex situ means before installation of the catalyst into the reactor; in situ means in the reactor (after the catalyst installation).

In one process variant, the catalyst can also be impregnated in situ with alkaline earth metal ions by adding alkaline earth metal ions, for example in the form of dissolved alkaline earth metal salts, to the solution of the aromatic substrate (reactant, here the compounds of the formulae (II) and/or (III)) to be hydrogenated. To this end, for example, the appropriate amount of salt is first dissolved in water and then added to the substrate dissolved in an organic solvent.

As a result of the preparation, the active metal is present in the coated catalysts usable with preference in accordance with the invention in the form of a metallic active metal.

As a result of the use of halogen-free, especially chlorine-free, active metal precursors and solvents in the preparation of the coated catalyst usable in accordance with the invention, the halide content, especially chloride content, of the inventive coated catalysts is additionally below 0.05% by weight (from 0 to <500 ppm by weight, for example in the range of 0-400 ppm by weight), based on the total weight of the catalyst.

The chloride content is determined by ion chromatography, for example with the method described below.

In this document, all ppm data are understood to mean parts by weight (ppm by weight), unless stated otherwise.

In a selected variant, it is preferred that the percentage ratio of the $Q_2$ and $Q_3$ structures determined by means of $^{29}$Si solid-state NMR, $Q_2/Q_3$, is less than 25, preferably less than 20, more preferably less than 15, for example in the range from 0 to 14 or from 0.1 to 13. This also means that the degree of condensation of the silica in the support used is particularly high.

The $Q_n$ structures (n=2, 3, 4) are identified and the percentage ratio is determined by means of $^{29}$Si solid-state NMR.

$Q_n$=Si(OSi)$_n$(OH)$_{4-n}$ where n=1, 2, 3 or 4.

When n=4, $Q_n$ is found at −110.8 ppm, when n=3 at −100.5 ppm and when n=2 at −90.7 ppm (standard: tetramethylsilane) ($Q_0$ and $Q_1$ were not identified). The analysis is carried out under the conditions of magic angle spinning at room temperature (20° C.) (MAS 5500 Hz) with cross-polarization (CP 5 ms) and using dipolar decoupling of $^1$H. Owing to the partial overlapping of the signals, the intensities are evaluated by means of line shape analysis. The line shape analysis was carried out with a standard software package from Galactic Industries, by calculating a least squares fit iteratively.

The support material of the $SiO_2$ coated catalysts usable with preference in accordance with the invention preferably does not comprise more than 1% by weight and in particular not more than 0.5% by weight and in particular <500 ppm by weight of aluminum oxide, calculated as $Al_2O_3$.

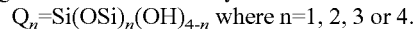

Since the condensation of silica can also be influenced by aluminum and iron, the total concentration of Al(III) and Fe(II and/or III) is preferably less than 300 ppm, more preferably less than 200 ppm, and is, for example, in the range from 0 to 180 ppm.

The proportion of alkali metal oxide results preferably from the preparation of the support material and can be up to 2% by weight. Frequently, it is less than 1% by weight. Also suitable are alkali metal oxide-free supports (0 to <0.1% by weight). The proportion of MgO, CaO, $TiO_2$ or of $ZrO_2$ may make up up to 10% by weight of the support material and is preferably not more than 5% by weight. However, suitable support materials are also those which do not comprise any detectable amounts of these metal oxides (from 0 to <0.1% by weight).

Because Al(III) and Fe(II and/or III) can give rise to acidic sites incorporated into silica, it is preferred that charge compensation is present in the carrier, preferably with alkaline earth metal cations ($M^{2+}$, M=Be, Mg, Ca, Sr, Ba). This means that the weight ratio of M(II) to (Al(III)+Fe(II and/or III)) is greater than 0.5, preferably >1, more preferably greater than 3.

The Roman numerals in brackets after the element symbol mean the oxidation state of the element.

Alternatively to the above-described coated catalysts which have an $SiO_2$ support, it is possible as already mentioned at the outset to use supported catalysts which have an $Al_2O_3$ support. Such catalysts which comprise Ru as an active metal on an $Al_2O_3$ support are disclosed, for example, in EP 0 814 098 A1 and in WO 99/32427, to which explicit reference is made on this subject and whose disclosure on this subject is considered to form part of the present disclosure.

The process according to the invention is also performed in the presence of hydrogen. Useful reaction gases are, as well as hydrogen, also hydrogenous gases which do not comprise any catalyst poisons such as carbon monoxide or sulfur-containing gases such as $H_2S$ or COS, for example mixtures of hydrogen with inert gases such as nitrogen, or reformer off-gases which typically also comprise volatile hydrocarbons. Preference is given to using pure hydrogen (purity ≥99.9% by volume, particularly ≥99.95% by volume, especially ≥99.99% by volume). In this case, hydrogen or the selected hydrogenous gas is generally likewise introduced continuously into each of the hydrogenation reactors used.

The process according to the invention for preparing the cycloaliphatic compounds of the formula (I), preferably 4-isopropylcyclohexylmethanol of the formula (Ia) or (Ib) and (Ic), is performed in the presence of hydrogen and in the presence of a catalyst which comprises, as an active metal, ruthenium applied to a support, the support comprising $Al_2O_3$ and/or $SiO_2$ and the catalyst being used in the form of a fixed bed catalyst in a hydrogenation reactor or in a plurality of hydrogenation reactors connected in series.

The process according to the invention can accordingly, as desired, be carried out in one hydrogenation reactor or in a plurality of hydrogenation reactors connected in series. Preference is given to performing the hydrogenation process according to the invention in a cascade of a plurality of, more preferably in a cascade of from 2 to 5, hydrogenation reactors connected in series.

The inventive hydrogenation is performed continuously. Suitable reactors, i.e. hydrogenation reactors, include trickle reactors or those which can be operated in flooded mode (liquid phase mode) by the fixed bed method. The hydrogen can be passed over the catalyst either in cocurrent with the solution of the reactant to be hydrogenated or in countercurrent.

Suitable apparatus for performing a hydrogenation after the hydrogenation over the fixed catalyst bed are known from the prior art, for example from Ullmanns Enzyklopädie der Technischen Chemie, 4th edition, Volume 13, p. 135 ff., and from P. N. Rylander, "Hydrogenation and Dehydrogenation" in Ullmann's Encyclopedia of Industrial Chemistry, 5th ed. on CD-ROM.

The inventive hydrogenation can be carried out in only one hydrogenation reactor or in a cascade of a plurality of, preferably from 2 to 5, more preferably from 2 to 4, most preferably 2 or 3 and especially preferably 2, hydrogenation reactors connected in series. The term "connected in series" is understood here and in the context of the overall present disclosure to mean that a plurality of hydrogenation reactors are connected to one another in such a way that the output of the first or of an upstream reactor, in the sense of a cascade or series connection, is connected to the input of the second hydrogenation reactor or of the hydrogenation reactor immediately downstream in each case.

The reactors mentioned may, as described above, be operated independently of one another in trickle mode or in flooded mode (liquid phase mode). It is also possible to operate the hydrogenation reactors connected in series in a cascade in different modes. For example, the first or the first few, preferably the first two, hydrogenation reactors can be operated in trickle mode and the last reactor in liquid phase mode.

The individual reactors may each independently be operated with complete or partial recycling of the reaction mixture discharged from the reactor. In a preferred embodiment, at least one of the hydrogenation reactors used, more preferably at least one of the hydrogenation reactors operated in trickle mode, is operated with partial recycling of the reaction mixture discharged.

The individual reactors can alternatively also each independently be operated in so-called straight pass, i.e. without complete or partial recycling of the reaction mixture discharged from the reactor. In a preferred embodiment, at least one of the hydrogenation reactors used, more preferably at least one of the hydrogenation reactors operated in liquid phase mode, is operated in straight pass.

In a preferred embodiment, the process according to the invention is performed in such a way that the catalyst is used in the form of a fixed bed catalyst in a hydrogenation reactor or a plurality of hydrogenation reactors connected in series, wherein
   a) the starting compounds of the formula (II) and/or (III) and hydrogen are introduced continuously into the (first) hydrogenation reactor,
   b) the resulting reaction mixture comprising 1-hydroxyalkylcyclohexane of the formula (I) is discharged continuously from the (first) hydrogenation reactor and, if desired, partly recycled back into the (first) hydrogenation reactor and
   c) if desired, the 1-hydroxyalkylcyclohexane of the formula (I) is removed from the reaction mixture which has been discharged from the (first) hydrogenation reactor in step b) and not recycled.

The process according to the invention is performed continuously, in which case, in a first step a), the starting compound or starting compounds of the formula (II) and/or (III), preferably cuminaldehyde of the formula (IIa) and hydrogen, are introduced continuously into a hydrogenation reactor or into a first hydrogenation reactor, i.e. are fed continuously thereto. The hydrogenation reactor comprises the fixed bed catalyst as described above and can be operated in liquid phase mode or in trickle mode as described above, preferably in trickle mode.

In this way, the complete or partial conversion to the desired reaction product of the formula (I) is effected. This reaction product is discharged continuously from the hydrogenation reactor or from the first hydrogenation reactor in process step b) in the form of a reaction mixture which may comprise as yet unconverted reactant or else incompletely hydrogenated intermediates. If desired, the reaction mixture which comprises 1-hydroxyalkylcyclohexane of the formula (I), preferably 4-isopropylcyclo-hexylmethanol of the formula (Ia), and is discharged from the hydrogenation reactor or from the first hydrogenation reactor in step b) can partly be recycled back into said hydrogenation reactor, i.e. the particular hydrogenation reactor can also be operated in "circulation" or in "loop mode".

It is accordingly possible to recycle a portion of the reaction mixture discharged back into the same hydrogenation reactor and to introduce the remaining portion continuously into a further hydrogenation reactor. In this way, it is possible, especially in the case of different reaction conditions in the individual hydrogenation reactors, to control and to influence the course of the reaction in the desired manner.

In the optional process step c), if desired, the 1-hydroxyalkylcyclohexane of the formula (I) is removed from the reaction mixture which has been discharged from the hydrogenation reactor or from the first hydrogenation reactor in step b) and not recycled back. In this way, the desired target compounds can be obtained in high purity. The removal of the desired target compound of the formula (I), preferably 4-isopropylcyclohexylmethanol of the formula (Ia), can be carried out, for example, by suitable distillation methods, as known to those skilled in the art. In the case of complete or very substantial hydrogenation of the starting materials used, and in the case of a low degree of formation of by-products and in the absence of solvents, a reaction mixture or product which consists to a high degree, often to an extent of 90% by weight or higher, preferably to an extent of 95% by weight or higher, more preferably to an extent of from 95 to 99.5% by weight, of the desired 1-hydroxyalkylcyclohexane of the formula (I) is already obtained in step b). In these cases, if desired, the optional removal in step c) can be omitted.

In a particularly preferred embodiment, the hydrogenation process according to the invention is undertaken in such a way that the catalytic hydrogenation is performed in a cascade of n hydrogenation reactors connected in series, where n is an integer from 2 to 5, and where
   a1) the reaction mixture which has been discharged continuously from an upstream hydrogenation reactor and not recycled, and hydrogen, are introduced continuously into the downstream hydrogenation reactor,
   b1) the resulting reaction mixture comprising 1-hydroxyalkylcyclohexane of the formula (I) is discharged continuously from the particular hydrogenation reactor and, if desired, partly recycled back into the particular hydrogenation reactor, and
   c1) if desired, the 1-hydroxyalkylcyclohexane of the formula (I) is removed from the reaction mixture which has been discharged from the nth hydrogenation reactor in step b1) and not recycled.

It is obvious that, as described above under step a), the starting compounds of the formula (II) and/or (III) and hydrogen are introduced continuously into the first hydrogenation reactor and, as described above under step b), the resulting reaction mixture comprising 1-hydroxyalkylcyclohexane of the formula (I) is discharged continuously from the first hydrogenation reactor and, if desired, recycled partly back into the (first) hydrogenation reactor.

The index n is preferably an integer from 2 to 4, more preferably 2 or 3 and especially preferably 2, corresponding to from 2 to 4, more preferably 2 or 3 and especially preferably 2 hydrogenation reactors connected in series. In the context of this embodiment, the term "upstream hydrogenation reactor" is understood to mean either the first or another hydrogenation reactor in the cascade of n hydrogenation reactors, excluding the nth, i.e. last, hydrogenation reactor of the cascade. The term "downstream hydrogenation reactor" is understood to mean the hydrogenation reactor which immediately follows an upstream reactor. Accordingly, the second hydrogenation reactor of the series of hydrogenation reactors would be understood to mean the "downstream" hydrogenation reactor of the first hydrogenation reactor. The third hydrogenation reactor would be understood to mean the "downstream" hydrogenation reactor of the second (upstream) hydrogenation reactor. Accordingly, all n hydrogenation reactors may, if desired, be operated with partial recycling of the reaction mixture obtained, i.e. in circulation or in loop mode. The individual hydrogenation reactors of the reactor cascade can, as desired, each be operated in liquid phase or trickle mode, and, as desired, with or without recycling of the resulting reaction mixtures.

In this particularly preferred embodiment of the process according to the invention, in step a1), the reaction mixture which has been discharged continuously from an upstream hydrogenation reactor, specifically the first hydrogenation reactor, and not recycled, and hydrogen, are introduced continuously into the downstream hydrogenation reactor. In step b1), the resulting reaction mixture comprising 1-hydroxyalkylcyclohexane of the formula (I) is discharged continuously from the particular hydrogenation reactor and partly recycled, if desired, back into the particular hydrogenation reactor. In step c1), if desired, the 1-hydroxyalkylcyclohexane of the formula (I) is removed from the reaction mixture which has been discharged in step b1) from the nth, i.e. last, hydrogenation reactor of the cascade and has not been recycled back.

All hydrogenation reactors provided in the cascade for use with preference in accordance with the invention are accordingly preferably operated such that the selected starting material or the reaction mixture obtained in an upstream hydrogenation reactor is introduced continuously into the particular hydrogenation reactor and the reaction mixture formed is discharged therefrom again continuously.

It has additionally been found to be advantageous that the first hydrogenation reactor of the reactor cascade, i.e. the reactor into which the selected starting materials of the formulae (II) and/or (III) are introduced, is operated in trickle mode.

It has additionally been found to be advantageous that the further hydrogenation reactor or at least one of the further hydrogenation reactors is operated in liquid phase mode. Especially preferably, the last hydrogenation reactor of the cascade of the hydrogenation reactors connected in series is operated in liquid phase mode.

The reaction mixture discharged from this last hydrogenation reactor consists frequently, as described above, to a high degree of the desired 1-hydroxyalkylcyclohexane of the formula (I), or, in the case of use of cuminaldehyde of the formula (IIa), of 4-isopropylcyclohexylmethanol of the formula (Ia). This allows the optional step of removing the process product from the resulting reaction mixture to be omitted, according to the requirements on the purity of the desired product.

In principle, it is possible, in the case of use of a cascade of two or more hydrogenation reactors, also to operate them with different supported Ru fixed bed catalysts among those described above. However, it has been found to be practicable and advantageous when the further hydrogenation reactor or the further hydrogenation reactors comprise(s) the same fixed bed catalyst as the first hydrogenation reactor. Preferably, all reactors of the reactor cascade comprise the same catalyst which comprises, as described above, Ru on an $Al_2O_3$ and/or $SiO_2$ support, preferably on an $SiO_2$ support.

In a preferred embodiment, the process according to the invention is performed in a cascade of 2 hydrogenation reactors, of which the first (main reactor) is operated in trickle mode. The second hydrogenation reactor (postreactor) connected downstream of the main reactor can either be operated in trickle mode or in liquid phase mode. Preference is given to operating the postreactor in liquid phase mode. Preferably in turn, the main reactor is operated in circulation, i.e. with partial recycling of the discharged reaction mixture, and the postreactor in straight pass, i.e. without recycling of the discharged reaction mixture.

In a further preferred embodiment, the process according to the invention is performed in a cascade of 3 hydrogenation reactors, of which the first and second (main reactor) are operated in trickle mode and the third in liquid phase mode. Preferably in turn, the first two reactors are operated in circulation, i.e. with partial recycling of the reaction mixture discharged in each case, and the postreactor in straight pass, i.e. without recycling of the discharged reaction mixture.

The actual hydrogenation is effected typically in analogy to the known hydrogenation processes for hydrogenating organic compounds which have hydrogenatable groups, preferably for hydrogenating a carbocyclic aromatic group to the corresponding carbocyclic aliphatic group (a so-called ring hydrogenation), as described in the prior art cited at the outset. To this end, the organic compound, as a liquid phase or gas phase, preferably as a liquid phase, is contacted with the fixed bed catalyst in the presence of hydrogen.

The inventive hydrogenation can be performed either at standard hydrogen pressure or at elevated hydrogen pressure, for example at an absolute hydrogen pressure of at least 1.1 bar, preferably at least 2 bar. In general, the absolute hydrogen pressure will not exceed a value of 325 bar and preferably 300 bar. More preferably, the absolute hydrogen pressure is in the range from 10 to 300 bar, even more preferably in the range from 50 to 250 bar and even more preferably in the range from 100 to 250 bar, especially preferably in the range from 125 to 250 bar and most preferably in the range from 125 to 200 bar (in each case absolute).

The hydrogenation process according to the invention can be performed in the absence of a solvent or diluent or else in the presence of a solvent or diluent, i.e. it is not necessary to perform the hydrogenation in solution.

The solvent or diluent used may be any suitable solvent or diluent. Useful solvents or diluents are in principle those which are capable of very substantially dissolving the organic compound to be hydrogenated or mixed completely with it and are inert under the hydrogenation conditions, i.e. are not hydrogenated.

Examples of suitable solvents are cyclic and acyclic ethers, for example tetrahydrofuran, dioxane, methyl tert-butyl ether, dimethoxyethane, dimethoxypropane, dimethyl diethylene glycol, aliphatic alcohols such as methanol, ethanol, n- or isopropanol, n-, 2-, iso- or tert-butanol, carboxylic esters such as methyl acetate, ethyl acetate, propyl acetate or butyl acetate, and aliphatic ether alcohols such as methoxypropanol, and cycloaliphatic compounds such as cyclohexane, methylcyclohexane and dimethylcyclohexane.

The amount of the solvent or diluent used if desired is not particularly restricted and can be selected freely as required, although preference is given to those amounts which lead to a from 3 to 70% by weight solution of the organic compound intended for hydrogenation.

In the case of use of a solvent, particular preference is given in the process according to the invention to using the product formed in the hydrogenation, i.e. preferably the compounds of the formula (I), as a solvent, optionally in addition to other solvents or diluents or else in addition to intermediates or by-products of the hydrogenation, for example p-cymene, cumene, 1-isopropyl-4-methylcyclohexane (cis/trans) and isopropylcyclohexane. In each case, a portion of the product formed in the process can be added to the aromatic still to be hydrogenated.

In the process according to the invention, it is possible to dispense with the addition of further solvents, such as those described above. Accordingly, in a preferred embodiment of the hydrogenation process according to the invention, the hydrogenation is performed without addition of solvents (apart from the intermediates and by-products mentioned).

The reaction temperatures in the process according to the invention are generally at least 30° C. and frequently will not exceed a value of 250° C. Preference is given to performing the hydrogenation process according to the invention at temperatures in the range from 50 to 200° C., more preferably from 70 to 200° C. and even more preferably in the range from 80 to 180° C., and especially preferably in the range from 80 to 160° C., even more preferably to 140° C.

It is obvious that, in the case of use of a plurality of hydrogenation reactors connected in series, they can be operated at different pressures and different temperatures.

Owing to the high catalyst activity, comparatively small amounts of catalyst are required, based on the reactant used. In the inventive continuous configuration of the hydrogenation process, the reactant of the formula (II) or (III) to be hydrogenated, or the reaction mixture discharged from an upstream hydrogenation reactor, will typically be conducted over the catalyst in an amount of from 0.05 to 3 kg/(l (catalyst)·h), preferably from 0.1 to 2 kg/(l(catalyst)·h), especially preferably from 0.1 to 1.0 kg/(l(catalyst)·h) and most preferably from 0.1 to 0.6 kg/(l(catalyst)·h).

It will be appreciated that the catalysts used in this process, in the event of declining activity, can be regenerated by methods which are customary for noble metal catalysts such as ruthenium catalysts and are known to those skilled in the art. Mention should be made here, for example, of the treatment of the catalyst with oxygen as described in BE 882 279, treatment with dilute halogen-free mineral acids as described in U.S. Pat. No. 4,072,628, or treatment with hydrogen peroxide, for example in the form of aqueous solutions with a content of from 0.1 to 35% by weight, or treatment with other oxidizing substances, preferably in the form of halogen-free solutions. Typically, the catalyst, after reactivation and before reuse, will be rinsed with a solvent, for example water.

When one or more of the hydrogenation reactors used in accordance with the invention are operated with partial recycling of the reaction mixture discharged in each case, i.e. in circulation or in loop mode, the quantitative ratio of amount introduced to amount recycled in the particular hydrogenation reactors (circulation/feed) is from about 1:1 to about 20:1, preferably from about 2:1 to about 15:1 and more preferably from about 3:1 to about 8:1.

In the case of use of the aldehydes preferred as starting materials in accordance with the invention, i.e. in the case of use of the compounds of the formula (II) in which the $R^2$ radical is hydrogen, more preferably in the case of use of cuminaldehyde of the formula (IIa), it has been found to be advantageous when they have a minimum acid number in the range from 0 to 5 mg KOH/g, preferably up to 4, and more preferably in the range from 0 to 3 mg KOH/g. In the case of aldehydes of the formula (II) for use in accordance with the invention which have a higher acid number, it has been found to be advantageous to treat them by adding the necessary amount of a base, such as preferably aqueous potassium hydroxide (KOH) solution or sodium hydroxide solution, as known to those skilled in the art.

The hydrogenation process according to the invention is a selective process for hydrogenating organic compounds which comprise hydrogenatable groups, preferably for hydrogenating a carbocyclic aromatic group to the corresponding carbocyclic aliphatic group, with which high yields and space-time yields, [amount of product/(catalyst volume·time)](kg/($l_{cat.}$·h)), [amount of product/(reactor volume·time)](kg/($l_{reactor}$·h)), based on the catalyst used, can be achieved, and in which the catalysts used can be used repeatedly for hydrogenations without workup. In particular, long catalyst lifetimes are achieved in the hydrogenation process according to the invention.

In addition, the hydrogenation process according to the invention opens up a high-performance route, which is suitable for conversions on the industrial scale, to isomer mixtures of the diastereomeric cycloaliphatic compounds mentioned, of the formula (Ib)

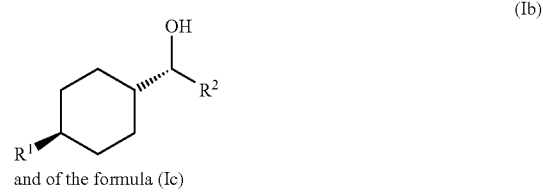

and of the formula (Ic)

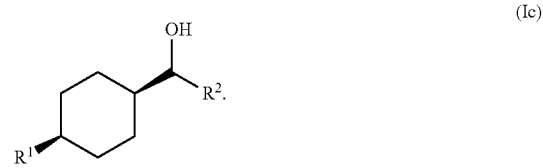

In the process according to the invention, the stereoisomers mentioned are generally obtained in the form of mixtures of the particular cis and trans isomers, where the relative ratio of cis/trans is often in the range from 1.9:1 to 2.5:1, preferably in the range from 2.0:1 to 2.4:1, even more preferably in the range from 2.1:1 to 2.3:1 (ratios each in mol/mol).

This is of significance especially in the case of the inventive conversion of the cuminaldehyde of the formula (IIa), in which the trans isomer of the formula (Id)

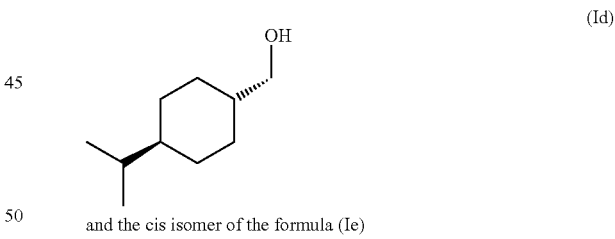

and the cis isomer of the formula (Ie)

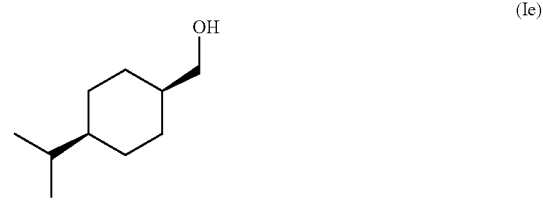

are obtained in the relative quantitative ratio described above. This is of significance especially with regard to utilization of the mixture thus obtained as an aroma chemical, since the stereoisomers mentioned differ significantly with regard to their odor impression.

The process according to the invention therefore provides a route, which is employable industrially in a particularly advantageous manner, to the isomer mixtures of the formulae (Id) and (Ie) which are very sought-after as aroma chemicals. The composition of the products obtainable in accordance with the invention, with regard to its cis/trans ratio, can be controlled within the above ranges through suitable selection of the reaction conditions in the individual hydrogenation reactions, which frequently allows a subsequent enrichment or depletion, for example by complicated distillative separation methods, to be dispensed with.

The examples which follow serve to illustrate the invention, but without restricting it in any way:

Example 1

Preparation of an SiO2-Supported Ruthenium Catalyst 50 kg of an $SiO_2$ support (D11-10 (BASF SE); 3 mm extrudates, water absorption of 0.95 ml/g, BET 135 $m^2/g$) were initially charged in an impregnating drum and impregnated at water absorption 96 to 98% by weight. The aqueous impregnation solution comprised 0.176 kg of Ru as ruthenium acetate (Umicore, 4.34% by weight of Ru). The impregnated catalyst was dried without motion at an oven temperature of 145° C. down to a residual moisture content of approximately 1%. The reduction in hydrogen was effected with motion (approximately 75% $H_2$ in $N_2$, using $N_2$ as the purge stream; 1.5 $m^3$ (STP)/h of $H_2$-0.5 $m^3$ (STP)/h of $N_2$) with a moving bed at 300° C. and a residence time of 90 minutes (1-2 h). The passivation was effected in dilute air (air in $N_2$). The addition of air was regulated such that the temperature of the catalyst remained below 30 to 35° C. The finished catalyst comprised 0.31 to 0.32% by weight of Ru.

Example 2

A continuous plant consisting of two tubular reactors connected in series (main reactor 150 ml and postreactor 100 ml) was charged with the catalyst prepared according to example 1 (main reactor: 58 g, postreactor: 38 g). The main reactor was operated in trickle mode with circulation (circulation/feed=100/1), the postreactor in straight pass in liquid phase mode. The cuminaldehyde (47 g/h) was pumped through the reactor cascade with pure hydrogen at a mean temperature of 125° C. in the main reactor and 110° C. in the postreactor and a pressure of 200 bar. The catalyst hourly velocity was 0.31 $kg_{cuminaldehyde}/l_{cat.} \times h$. The gas chromatography analysis (GC column: RTX 35, length 30 m, diameter 0.25 μm; temperature program: from 80° C. at 2° C./min to 120° C., from 120° C. to 250° C. at 5° C./min) of the reaction effluent showed that the cuminaldehyde had been converted to an extent of 100% and also that the cumin alcohol intermediate was no longer detectable by gas chromatography in the output mixture. The selectivity of cis/trans-4-isopropylcyclohexylmethanol was 90.7 area %. The secondary components detected were approx. 9 area % of low boilers (components with a lower boiling point than 4-isopropylcyclohexylmethanol, for example p-cymene, cumene, 1-isopropyl-4-methylcyclohexane (cis/trans) and isopropylcyclohexane). The cis/trans ratio of the resulting 4-isopropyl-cyclohexylmethanol was 2.20:1.

Example 3 (Comparative Example)

In a 300 ml pressure reactor, 4.5 g of the catalyst prepared according to example 1 were initially charged in a catalyst insert basket and admixed with 150 g of cuminaldehyde. The hydrogenation was carried out with pure hydrogen at a constant pressure of 200 bar and a temperature of 180° C. Hydrogenation was continued until no further hydrogen was absorbed (35 hours). The reactor was subsequently decompressed. The conversion of cuminaldehyde was 100%, and the cumin alcohol intermediate was no longer detectable by gas chromatography in the output mixture (GC column: RTX 35, length 30 m, layer thickness 0.25 μm; temperature program: from 80° C. at 2° C./min to 120° C., from 120° C. at 5° C./min to 250° C.). The selectivity of cis/trans-4-isopropylcyclohexylmethanol was 87.5 area %. The secondary components detected were approx. 11.5 area % of low boilers (components with a lower boiling point than 4-isopropylcyclohexylmethanol, for example p-cymene, cumene, 1-isopropyl-4-methylcyclohexane (cis/trans) and isopropylcyclohexane). The cis/trans ratio of the resulting 4-isopropylcyclohexylmethanol was 1.86:1.

The invention claimed is:

1. A continuous process for preparing a 1-hydroxyalkylcyclohexane of the formula (I)

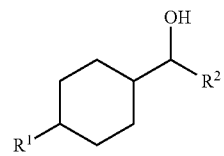

(I)

where
$R^1$ is isopropyl and
$R^2$ is hydrogen or a straight-chain or branched alkyl radical having from 1 to 3 carbon atoms, which comprises catalytically hydrogenating an aromatic carbonyl compound of the formula (II)

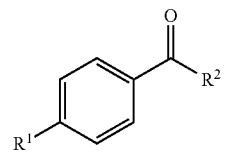

(II)

and/or by catalytically hydrogenating an aromatic alcohol of the formula (III)

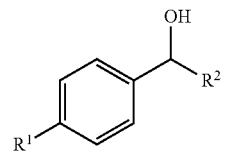

(III)

in which the $R^1$ and $R^2$ radicals are each as defined in formula (I),
in the presence of hydrogen and in the presence of a catalyst which comprises, as an active metal, ruthenium applied to a support, the support comprising $SiO_2$, and the catalyst being used in the form of a fixed bed catalyst in a hydrogenation reactor or in a plurality of hydrogenation reactors connected in series, and the fixed bed catalyst, based on the total weight of the finished catalyst, having a ruthenium content of from 0.1 to 0.5% by weight;

wherein the catalytic hydrogenation is performed in a cascade of n hydrogenation reactors connected in series comprising a first hydrogenation reactor and one or more further hydrogenation reactors, where n is an integer from 2 to 5, and where a1) the reaction mixture which has been discharged continuously from an upstream hydrogenation reactor and not recycled, and hydrogen, are introduced continuously into the downstream hydrogenation reactor, b1) the resulting reaction mixture comprising 1-hydroxyalkylcyclohexane of the formula (I) is discharged continuously from the particular hydrogenation reactor and optionally, partly recycled back into the particular hydrogenation reactor, and c1) optionally, the 1-hydroxyalkylcyclohexane of the formula (I) is removed from the reaction mixture which has been discharged from the nth hydrogenation reactor in step b1) and not recycled.

2. The process according to claim 1, wherein a) the starting compounds of the formula (II) and/or (III) and hydrogen are introduced continuously into the first hydrogenation reactor, b) the resulting reaction mixture comprising 1-hydroxyalkylcyclohexane of the formula (I) is discharged continuously from the first hydrogenation reactor and, if desired, partly recycled back into the first hydrogenation reactor and c) optionally, the 1-hydroxyalkylcyclohexane of the formula (I) is removed from the reaction mixture which has been discharged from the first hydrogenation reactor in step b) and not recycled.

3. The process according to claim 1, wherein an aromatic carbonyl compound of the formula (II) is used.

4. The process according to claim 1, wherein a fixed bed catalyst which comprises only $SiO_2$ as a support is used.

5. The process according to claim 1, wherein a fixed bed catalyst comprising, as an active metal, ruthenium alone or together with at least one further metal of transition groups IB, VIIB or VIII of the Periodic Table of the Elements, applied to a support comprising silicon dioxide as a support material, the amount of the active metal being <1% by weight, based on the total weight of the catalyst, and at least 60% by weight of the active metal being present in the coating of the catalyst up to a penetration depth of 200 µm, determined by means of SEM-EPMA, is used.

6. The process according to claim 1, wherein the hydrogenation is performed without addition of solvents.

7. The process according to claim 1, wherein the first hydrogenation reactor is operated in trickle mode.

8. The process according to claim 1, wherein at least one of the further hydrogenation reactors is operated in liquid phase mode.

9. The process according to claim 1, wherein the hydrogenation is performed at pressures in the range from 100 to 250 bar.

10. The process according to claim 1, wherein the hydrogenation is performed at temperatures in the range from 80 to 160° C.

11. The process according to claim 1, wherein an aromatic aldehyde of the formula (II) which has an acid value of from 0 to 5 mg KOH/g is used.

* * * * *